United States Patent [19]

Aoshima et al.

[11] Patent Number: 4,518,462
[45] Date of Patent: May 21, 1985

[54] DISTILLATION PROCESS FOR PURIFYING METHYL METHACRYLATE

[75] Inventors: Atsushi Aoshima, Yokohama; Yoshio Suzuki; Mikihiko Nakamura, both of Fuji, all of Japan

[73] Assignee: Asahi Kasei Kogyo Kabushiki Kaisha, Osaka, Japan

[21] Appl. No.: 497,783

[22] Filed: May 25, 1983

Related U.S. Application Data

[63] Continuation-in-part of Ser. No. 272,598, Jun. 11, 1981, abandoned.

[30] Foreign Application Priority Data

Jun. 20, 1980 [JP] Japan .................................. 55-83542
Jun. 20, 1980 [JP] Japan .................................. 55-83543

[51] Int. Cl.$^3$ .......................... B01D 3/36; C07C 67/54
[52] U.S. Cl. .......................................... 203/39; 203/15; 203/52; 203/68; 203/70; 203/81; 203/DIG. 19; 203/DIG. 21; 560/218
[58] Field of Search ............................ 203/52, 68–70, 203/66, 14, 15, 39, DIG. 21, 81, DIG. 19, 99; 560/218, 210; 568/913, 916

[56] References Cited

U.S. PATENT DOCUMENTS

| | | | |
|---|---|---|---|
| 2,406,561 | 8/1946 | Rehberg | 203/70 |
| 2,476,206 | 7/1949 | McCants | 203/68 |
| 2,561,680 | 7/1951 | Willke et al. | 203/70 |
| 2,581,789 | 1/1952 | Forman | 203/70 |
| 2,591,877 | 4/1952 | Robertson et al. | 203/68 |
| 3,239,572 | 3/1966 | Zinsstag | 203/70 |
| 3,431,181 | 3/1969 | Bouniot | 203/70 |
| 4,070,254 | 1/1978 | Sato et al. | 203/83 |

Primary Examiner—Wilbur Bascomb
Attorney, Agent, or Firm—Sprung Horn Kramer & Woods

[57] ABSTRACT

In purifying methyl methacrylate by feeding a feed mixture containing methanol, methyl methacrylate and 0.05 to 2% by weight, based on the weight of the methyl Methacrylate, of methyl isobutyrate to a first distillation column, subjecting the same to distillation therein in the presence of a saturated hydrocarbon having 6 or 7 carbon atoms while distilling out said saturated hydrocarbon, the methanol, a small amount of the methyl methacrylate and the methyl isobutyrate through the top of the first distillation column and simultaneously recovering methyl methacrylate freed from methanol and methyl isobutyrate from the bottom of the distillation column, wherein the top distillate is cooled in the decanter to be separated into two layers, the resulting upper layer composed mainly of the saturated hydrocarbon is returned to the first distillation column and the resulting lower layer composed mainly of methanol is fed to a second distillation column in which distillation is conducted while recovering the saturated hydrocarbon dissolved in the lower layer together with a part of the methanol from the top of the second distillation column and sending the same to the decanter, and withdrawing methanol, methyl isobutyrate and a small amount of methyl methacrylate from the bottom of the second distillation column, the methyl methacrylate can be effectively purified in high yield by allowing the saturated hydrocarbon to be present only above the feed stage of the first distillation column to which the feed mixture is fed, cooling the top distillate of the first distillation column to 0°–13° C. in the decanter, providing distillation stages above the feed stage of the second distillation column and conducting distillation while returning a part of the top distillate of the second distillation column to the top of the second distillation column, thereby separating methanol and methyl isobutyrate from methyl methacrylate.

5 Claims, 1 Drawing Figure

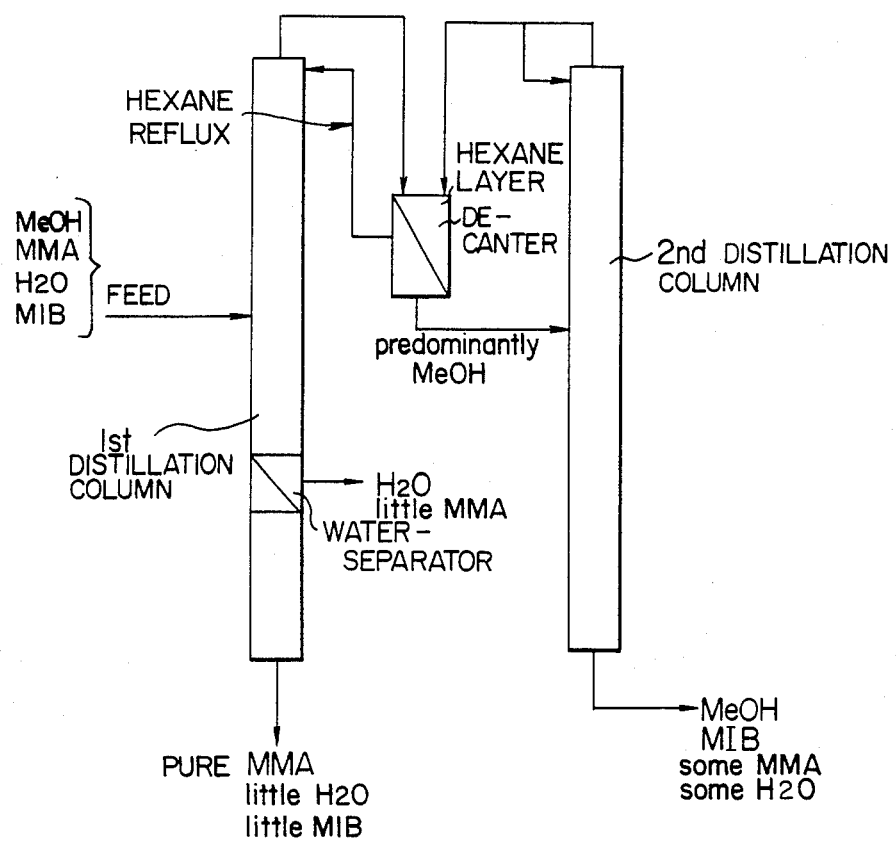

DISTILLATION PROCESS FOR PURIFYING METHYL METHACRYLATE

CROSS-REFERENCE TO RELATED APPLICATIONS

This is a continuation-in-part of application Ser. No. 272,598 filed June 11, 1981, and now abandoned.

BACKGROUND OF THE INVENTION

1. Field of the Invention

The present invention relates to a process for purifying methyl methacrylate, and more particularly to a process for purifying the same by distilling a mixture containing methanol, methyl methacrylate, a small amount of methyl isobutyrate and optionally water to remove the methanol and the methyl isobutyrate, or to remove the methanol, the methyl isobutyrate and the water.

2. Description of the Prior Art

As the process for producing methyl methacrylate, there have been known the acetonecyanhydrin process and the isobutylene (or t-butanol) oxidation process. The latter process includes a process comprising oxidizing isobutylene or t-butanol into methacrolein, further oxidizing the same into methacrylic acid, and then reacting the same with methanol into methyl methacrylate, and a process comprising reacting in one step methacrolein with oxygen and methanol to produce methyl methacrylate.

The reaction products obtained in the preparation of methyl methacrylate by esterifying methacrylic acid with a large excess of methanol or by oxidizing methacrolein with oxygen in methanol contain methanol in an amount as large as 20 to 85% by weight and form a homogeneous phase in many cases. Although the excess methanol is usually separated, recovered and reused in the reaction, the extraction of methanol with water from said homogenous mixture requires a large amount of water, resulting in economical disadvantages such as an increased amount of materials to be treated, an increased utility cost for recovering methanol from the water-methanol solutions, and the like. In addition, the above feed mixture forms a complicated azeotropic mixture, so that it is difficult to separate and purify methyl methacrylate from said feed mixture by mere distillation.

On the other hand, a method of the extraction of methyl methacrylate in the presence of a hydrocarbon and water from the above feed mixture is known as another method for isolating methyl methacrylate from the feed mixture. This method is, however, troublesome because it requires the recovery of methyl methacrylate from the hydrocarbon and of methanol from the water-methanol solution.

Moreover, the reaction mixtures obtained by these processes for preparing methyl methacrylate contain a variety of impurities originated from the raw materials and from side reactions. In particular, when methyl isobutyrate is contained as an impurity, the separation thereof is markedly difficult even by means of distillation, extraction, or the like because the boiling point of methyl isobutyrate (92.3° C.) is very close to that of the objective methyl methacrylate (100.3° C.) and the difference between the two in solubilities in water and other solvents is also small. Therefore, the conventional process requires a complicated process for the separation and also requires a utility such as much steam or the like for the separation. On the other hand, if methyl isobutyrate is present in the methyl methacrylate, it follows that in the polymeric products obtained by polymerizing the methyl methacrylate, there remains the methyl isobutyrate which does not participate in the polymerization, and this results in a deterioration of the quality of the polymeric product. Therefore, it is essential to remove this impurity even though the step therefor is complicated.

As an example of the known separation process, Japanese Patent Application Kokai (Laid-Open) No. 146,418/76 proposes a method which comprises distilling a crude methacrylate containing an isobutyrate in the presence of a small amount of water, separating the distillate into the organic phase and the aqueous phase, and further distilling said organic phase in the presence of water to concentrate and remove the isobutyrate. However, according to this proposal, it is necessary to form two liquid phases of water and organic matter at the top of a distillation column, and therefore, when a large amount of methanol or the like is present a single uniform phase is formed. Therefore, only a minute amount of methanol is allowed to co-exist, and these water-soluble organic matters must be previously removed to obtain crude methacrylate free from the water-soluble organic matters.

However, as mentioned above, the reaction product obtained in the preparation of methyl methacrylate by esterifying methacrylic acid with an excess of methanol or by oxidizing methacrolein with oxygen in methanol contains methanol in an amount as large as 20 to 85% by weight, and the content of methyl isobutyrate in the reaction product usually comes to 0.05 to 2% by weight based on the weight of methyl methacrylate. When it is intended to separate methyl isobutyrate by distillation from said feed mixture the methyl isobutyrate and the methyl methacrylate both form azeotropic mixtures with methanol and water, and hence, it is substantially impossible to remove the methyl isobutyrate from the methyl methacrylate by distillation. As a method of separating and purifying methyl methacrylate from said feed mixture, there is also known a method of extracting methyl methacrylate with a hydrocarbon. However, the methyl isobutyrate is difficult to remove from methyl methacrylate because the extraction of the methyl isobutyrate with a hydrocarbon is easy equally to or easier than that of the methyl methacrylate.

SUMMARY OF THE INVENTION

The present inventors have conducted extensive research for finding a method for purifying methyl methacrylate from such a mixture containing a large amount of methanol by separating the methanol or both the methanol and the water and simultaneously separating simply the methyl isobutyrate from the methyl methacrylate, and as a result, it has been found that when the distillation is conducted in the first distillation column while allowing a saturated hydrocarbon having 6 or 7 carbon atoms to be present only above the feed stage to which the feed mixture is fed, cooling the top distillate containing the saturated hydrocarbon, methanol, a small amount of methyl methacrylate and methyl isobutyrate to 0°–13° C. in a decanter to separate it into two layers, returning the upper layer composed mainly of saturated hydrocarbon to the first distillation column, feeding the lower layer composed mainly of methanol to a second distillation column having distillation stages above the feed stage, and distillation is conducted in the second distillation column with reflux to distil out the saturated hydrocarbon dissolved in the layer composed mainly of methanol, together with a part of the methanol from the top and return it to the decanter, thereby obtaining methanol from the bottom of the second distillation column, the methyl isobutyrate is distilled out in the concentrated form in a small amount of methyl methacrylate from the top of the first distillation column, and a part of the methyl isobutyrate and the small amount of methyl methacrylate is distributed into the methanol layer of the separated saturated hydrocarbon-methanol layers, and when this methanol layer is subjected to distillation in the second distillation column while allowing said saturated hydrocarbon to be sufficiently present even below the feed stage, the methyl isobutyrate and the small amount of methyl methacrylate contained in the methanol layer are obtained from the bottom of the second distillation column together with methanol, whereby methanol and methyl isobutyrate or methanol, water and methyl isobutyrate are separated from the methyl methacrylate, thus the methyl methacrylate is purified.

According to this invention, there is provided a process for purifying methyl methacrylate by feeding a feed mixture containing methanol, methyl methacrylate and 0.05 to 2% by weight, based on the weight of the methyl methacrylate, of methyl isobutyrate (said mixture may be a gas mixture, a liquid mixture or a gas-liquid mixture) to a first distillation column, subjecting the same to distillation therein in the presence of a saturated hydrocarbon having 6 or 7 carbon atoms while distilling out said saturated hydrocarbon, the methanol, a small amount of the methyl methacrylate and the methyl isobutyrate through the top of the first distillation column and simultaneously recovering methyl methacrylate freed from methanol and methyl isobutyrate from the bottom of the distillation column, wherein the top distillate is cooled in a decanter to be separated into two layers, the resulting upper layer composed mainly of the saturated hydrocarbon is returned to the first distillation column and the resulting lower layer composed mainly of methanol is fed to a second distillation column in which distillation is conducted while recovering the saturated hydrocarbon dissolved in the lower layer together with a part of the methanol from the top of the second distillation column and sending the same to the decanter, and withdrawing methanol, methyl isobutyrate and a small amount of methyl methacrylate from the bottom of the second distillation column, characterized in that the saturated hydrocarbon is present only above the feed stage of the first distillation column to which the feed mixture is fed, the top distillate of the first distillation column is cooled to 0°–13° C. in the decanter, distillation stages are provided above the feed stage of the second distillation column and distillation is conducted while returning a part of the top distillate of the second distillation column to the top of the second distillation column, thereby separating methanol and methyl isobutyrate from methyl methacrylate, or a process for purifying methyl methacrylate by feeding a feed mixture containing methanol, methyl methacrylate, water and 0.05 to 2% by weight, based on the weight of the methyl methacrylate, of methyl isobutyrate to a first distillation column, subjecting the same to distillation therein in the presence of a saturated hydrocarbon having 6 or 7 carbon atoms while distilling out said saturated hydrocarbon, the methanol, a small amount of the methyl methacrylate and the methyl isobutyrate through the top of the first distillation column and simultaneously separating the bottom stream into a layer composed mainly of methyl methacrylate and a layer composed mainly of water, and withdrawing this water layer to recover methyl methacrylate, wherein the top distillate is cooled in a decanter to be separated into two layers, the resulting upper layer composed mainly of the saturated hydrocarbon is returned to the first distillation column and the resulting lower layer composed mainly of methanol is fed to a second distillation column in which distillation is conducted while recovering the saturated hydrocarbon dissolved in the lower layer together with a part of the methanol from the top of the second distillation column and sending the same to the decanter, while withdrawing methanol, methyl isobutyrate and a small amount of methyl methacrylate from the bottom of the second distillation column, characterized in that the saturated hydrocarbon is present only above the feed stage of the first distillation column to which the feed mixture is fed, the top distillate of the first distillation column is cooled to 0°–13° C. in the decanter, distillation stages are provided above the feed stage of the second distillation column and distillation is conducted while returning a part of the top distillate of the second distillation column to the top of the second distillation column, thereby separating methanol and methyl isobutyrate from methyl methacrylate.

BRIEF DESCRIPTION OF THE DRAWINGS

The accompanying drawing is a block diagram showing the distillation system of Example 2.

DETAILED DESCRIPTION OF THE INVENTION

In this invention, an entrainer that forms an azeotropic mixture preferentially with methanol is used to distil out methanol from the top of the column. In the distillation in which a saturated hydrocarbon having 6 or 7 carbon atoms is used as the entrainer, when the amount of said saturated hydrocarbon present in the column (hereinafter, in some cases, referred to as the first distillation column) is so sufficient that the saturated hydrocarbon may also be present in a significant amount below the feed stage, the amount of methyl methacrylate distilled out through the top decreases until substantially no methyl methacrylate is distilled out though the amount of water distilled out from the top is increased. As a consequence, the water content in the methanol obtained by separating the saturated hydrocarbon from said distillate is increased. In addition, methyl isobutyrate, when contained in the feed mixture, is scarcely distilled out along with methanol under such conditions. In controlling until what stage from the top the saturated hydrocarbon is allowed to be substantially present in response to the distillation conditions, the composition of feed, and the number of plates in the enriching section and the like, the control of the amount of the said hydrocarbon present in the column so that substantially the whole amount of the hydrocarbon is present only above the feed stage results in reduction of the amount of water distilled out through the top. On the other hand, the amount of methyl methacrylate distilled out increases somewhat, and it follows that a small amount of methyl methacrylate is distilled out from the top, and the amount of methyl isobutyrate is greatly increased to obtain a highly concentrated methyl isobutyrate solution in a small amount of methyl methacrylate. According to the present process, when the methyl isobutyrate content in the feed is 0.05 to 2% by weight based on the weight of methyl methacrylate, the proportion of methyl isobutyrate to methyl methacrylate in the distillate can be increased to 1 to 50% by weight, though it depends upon the number of plates of the column and the reflux ratio.

That is to say, in the case where substantially the whole amount of the saturated hydrocarbon is present only above the feed stage, the degree of distillation of methyl isobutyrate is increased as compared with those in the case where the amount of the hydrocarbon is so sufficient that the hydrocarbon is present in a significant amount even below said stage, and it becomes possible in the former case to separate methyl isobutyrate from methyl methacrylate. Contrary to methyl isobutyrate, water is difficult to distil out when substantially the whole amount of the hydrocarbon is present only above the feed stage, and accordingly, the water content in the methanol recovered by removing the hydrocarbon from the distillate becomes small. Where the recovered methanol is used again in the reaction, particularly in the method of the oxidation of methacrolein in methanol into methyl methacrylate, it is preferred that the water content is smaller. Since the reaction tends to be hindered more greatly as the water content increases, it is important for the reuse of the recovered methanol that the water content in the recovered methanol is decreased by suppressing the distillation of water as much as possible in the manner that substantially the whole amount of the saturated hydrocarbon is present only above the feed stage during the distillation, though the results may vary depending upon the kind of saturated hydrocarbon used.

In order to obtain the effect of this invention, the kind of saturated hydrocarbon and the distribution thereof in the column are very important. As the saturated hydrocarbon, those having 6 or 7 carbon atoms are preferable, and those having boiling points within the range of 65° to 100° C. are particularly preferable. Specifically, there may be mentioned hexane, cyclohexane, heptane, methylcyclopentane, dimethylpentane and the like. These may be used alone or in admixture. Such a saturated hydrocarbon serves to break the azeotropic mixture between methanol and methyl methacrylate and is therefore effective in separating the methanol from the methyl methacrylate. In addition, said saturated hydrocarbon has the effect that the relative volatility of water is lowered by allowing substantially the whole amount of the hydrocarbon to be present only above the feed stage as compared with the case of allowing the hydrocarbon to be present sufficiently even below the feed stage and that the amount of water distilled out is decreased.

Furthermore, when the feed mixture contains methyl isobutyrate, the distillation under such conditions increases the relative volatility between methyl isobutyrate and methyl methacrylate, whereby the removal of the former from the latter can be made surprisingly favorable.

The use of a hydrocarbon having more than seven carbon atoms is undesirable because it has no adequate effect on the separation of methanol from methyl methacrylate and also gives an increased amount of water distilled out. On the other hand, the use of a hydrocarbon having less than six carbon atoms results in a disadvantage of requiring, for distillation, a remarkably large amount of energy because of a low concentration of methanol in the distillate.

In the case of water being present in the feed to the first distillation column, when substantially the whole amount of the methanol is distilled out through the top, substantially no methanol is present in the lower part of the column, but water is present therein. Therefore, phase separation takes place between water and methyl methacrylate. Accordingly, the bottom liquid can be separated into two layers of an aqueous layer composed mainly of water and an organic layer composed mainly of methyl methacrylate, and the methyl methacrylate can be separated and purified by removing the aqueous layer.

In order to obtain methyl methacrylate by effecting the distillation in such a manner that a highly concentrated methyl isobutyrate solution in a small amount of methyl methacrylate is distilled out from the top, or alternatively, a highly concentrated methyl isobutyrate solution in a small amount of methyl methacrylate is distilled out from the top with distilling out substantially no water, thereby removing methanol together with methyl isobutyrate or removing methanol together with methyl methacrylate and water, it is important to select a preferable saturated hydrocarbon and control the amount of the saturated hydrocarbon present in the distillation column so that substantially the whole amount of the saturated hydrocarbon is present only above the feed stage.

When low-boiling compounds such as methacrolein and the like are contained in the feedstock to be used in this invention, it is recommendable to remove the same in advance by distillation along with a part of the methanol and then use the resulting mixture as the feed. Moreover, a polymerization inhibitor may be added to the feed mixture to prevent polymerization and the resulting mixture may be used as the feed.

As to the removal of the aqueous layer composed mainly of water from the bottom liquid of the first distillation column, when it is desired that the recovered methyl methacrylate be much more pure, the organic layer is fed to another distillation column while continuously withdrawing the aqueous layer, to distil minute amounts of water, methyl isobutyrate, methanol and low-boiling compounds present in the organic layer together with a part of the methyl methacrylate, and furthermore, this distillate may be fed to the reaction system before the first distillation column or to the purification system to take out further purified methyl methacrylate from the bottom. In this case, the operation conditions, particularly the operation pressure, of the two distillation columns may be varied to adjust the bottom temperature to a temperature at which methyl methacrylate is difficult to polymerize. When the feed contains methacrylic acid and/or its salt, a part or majority thereof may also be taken out of the system along with the removed water. It is also possible to carry out such an embodiment that the first distillation column is provided with a water-separator at the lower part, the aqueous layer is continuously taken out of the water-separator and methyl methacrylate is recovered from the bottom.

In recovering the hydrocarbon from the distillate of the first distillation column, the distillate is separated into a layer composed mainly of the hydrocarbon and another layer composed mainly of methanol, and the former layer is returned to the first distillation column. In this case, the amount of methanol dissolved in the hydrocarbon and the hydrocarbon content in the distillate of the first distillation column are factors for determining the reflux rate. However, these factors vary depending upon the kind of the hydrocarbon, and the amount of methanol dissolved in the hydrocarbon varies depending upon the temperatures of the layers separated. Usually, it is more advantageous to reduce the amount of methanol dissolved by cooling the layers. When the separated layers are cooled to 0°–13° C., the amount of the methanol dissolved in the saturated hydrocarbon layer is 6 to 10%, and when this hydrocarbon layer is refluxed, the reflux ratio of the first distillation column does not vary so greatly. However, when the temperature of the separated layers is higher than said range the amount of methanol dissolved in the hydrocarbon layer becomes large quickly, and since the separated hydrocarbon-methanol layers have incorporated thereinto a small amount of methyl methacrylate, methyl isobutyrate and slight amounts of other impurities in addition to the hydrocarbon and methanol, the amount of methanol dissolved in the hydrocarbon separated is larger than in the case of the mere hydrocarbon-methanol system. Accordingly, when the hydrocarbon layer having a larger methanol content is refluxed to the first distillation column, the refluxing ratio becomes larger, resulting in a disadvantage in respect of energy. In addition, the volatility of the small amount of methyl methacrylate and methyl isobutyrate which are distilled out from the top of the first distillation column together with the saturated hydrocarbon and the methanol becomes small, and hence, the amount of the methyl methacrylate and methyl isobutyrate distilled out decreases. Therefore, the amount of methyl methacrylate and methyl isobutyrate distributed into the methanol layer of the separated layers reduces, and the amounts of methyl methacrylate and methyl isobutyrate withdrawn along with methanol from the bottom of the second distillation column decrease, too, whereby it becomes impossible to effectively separate methyl isobutyrate from methyl methacrylate. Moreover, the distributing ratios of methyl methacrylate and methyl isobutyrate into the separated hydrocarbon and methanol layers in the decanter vary depending upon the temperature of the separated layers, and the higher the temperature the greater the distribution ratio into the hydrocarbon layer becomes. This also serves to reduce the amount of methyl methacrylate and methyl isobutyrate withdrawn from the bottom of the second distillation column, and plays an important role in the separation of methyl isobutyrate along with the effect on refluxing ratio of the amount of methanol dissolved in the hydrocarbon layer. The methanol layer separated is fed to the second distillation column, and the hydrocarbon dissolved therein is azeotropically distilled out along with a part of the methahol and then introduced into the decanter, whereby the hydrocarbon distilled out from the first distillation column is entirely returned to the first distillation column. The methyl isobutyrate distilled goes out of the system depending upon the composition of the distillate from the first distillation column and upon the method of separation into two layers, because the methyl isobutyrate distilled is easier to distribute to the methanol layer than to the hydrocarbon layer. In the first distillation column, methyl isobutyrate is distilled out through the top by allowing substantially the whole amount of the hydrocarbon to be present only above the feed stage and controlling the amount of the hydrocarbon present in the column. In the second distillation column, however, most of the methyl isobutyrate dissolved in the methanol layer can be withdrawn along with methanol from the bottom by effecting distillation under such conditions that the hydrocarbon is also present in a significant amount below the feed stage unlike the operation in the first distillation column. In order that the hydrocarbon is sufficiently present below the feed stage of the second distillation column, a part of the distillate from the top is returned to the top of the column to subject the column to refluxing to achieve said purpose. When the methanol layer is fed to the second distillation column, the feed stage may be any one of the middle stages, though it is necessary that the number of stages above the feed stage be enough to prevent the methyl isobutyrate contained in the fed methanol from being distilled out of the top of the column considering the reflux ratio. In a conventional azeotropic distillation, the feed to the second distillation column provided for the purpose of recovery of an entrainer is usually made near the top of the column. However, if the distillation is conducted under such conditions in the present invention, methyl isobutyrate is also distilled out along with the hydrocarbon and methanol from the top of the column, and becomes recycled between the first distillation column and the second distillation column, and it follows that the methyl isobutyrate is not withdrawn from the bottom of the second distillation column. Accordingly, in the present invention, the saturated hydrocarbon is allowed to be present only above the feed stage in the first distillation column, thereby distilling the methyl isobutyrate in the concentrated form relative to methyl methacrylate, and the separated layers are cooled and the distillation conditions in the second distillation column are made as mentioned above. By combining these conditions, the methyl isobutyrate can be obtained from the bottom of the second distillation column along with a small amount of methyl methacrylate and methanol. In other words, methyl isobutyrate can be separated and removed along with methanol from methyl methacrylate. The methanol thus recovered contains, besides methyl isobutyrate, a small amount of methyl methacrylate, or a small amount of methyl methacrylate and a minute amount of water. Methyl isobutyrate is removed from this methanol by distillation or by stripping employing an inert gas, and the methanol thus separated can be used again in the reaction. Since a part of the methyl methacrylate is also removed by entrainment at the removal of methyl isobutyrate, it is economically favorable to minimize the amount of methyl methacrylate in the methanol, namely, to minimize the amount of methyl methacrylate distilled out from the first distillation column.

As described above, according to the process of this invention, methyl methacrylate can be purified from a mixture of methanol, methyl methacrylate, a small amount of methyl isobutyrate and optionally water by easily and economically separating and removing the methanol and methyl isobutyrate or the methanol, methyl isobutyrate and water from the mixture.

DESCRIPTION OF THE PREFERRED EMBODIMENTS

This invention is illustrated more specifically below referring to Examples. However, the invention is not limited to the Examples. In the Examples, % and ppm are by weight unless otherwise specified.

EXAMPLE 1

A distillation system comprising a combination of the following first and second distillation columns was used in this Example: The first distillation column is an Oldershaw type column having 50 plates, in which an upper section having an inner diameter of 80 mm and 20 plates is combined with a lower section having an inner diameter of 50 mm and 30 plates. Said column is provided with a feed inlet at the 20th stage from the top and with a still at the 51st stage. It is also provided with a decanter to receive the distillate from the first column which decanter is a glass vessel equipped with a jacket for circulating a coolant. Said decanter is also equipped with a pipe and a pump through which the upper layer of the two layers separated in the decanter is returned to the first distillation column, and equipped with another means for sending the lower methanol layer of said two layers via a liquid level gauge by means of a regulated pump to the second distillation column, said level gauge being for maintaining the interface between said two layers at a constant level. The second distillation column is an Oldershaw type column having 50 plates and an inner diameter of 32 mm, and is provided with a feed inlet at the 20th stage from the top.

Hexane was present in said distillation system. The amount of hexane present in the first distillation column was controlled so as to keep the temperature of the 5th stage from the top at 60° C., and distillation was effected while supplying a feed mixture to the first distillation column at a rate of 854 g/hr, said feed mixture having a composition of 22.5% of methyl metahcrylate, 71.5% of methanol, 7.0% of water, and 420 ppm of methyl isobutyrate, and having added thereto 0.02% of hydroquinone and 0.03% of phenothiazine as polymerization inhibitors. During the distillation, the temperatures at the top, the feed stage, and the still of the first column were 50° C., 67° C., and 87° C., respectively, and hexane was not present below the feed stage. The temperatures at the top, the feed stage, and the bottom of the second distillation column were 50° C., 56° C., and 67° C., respectively. The reflux ratio of the second distillation column was set to 1.0. The temperature of the decanter for separating two layers was kept at 6° C. by circulating a coolant, and methanol containing 5% of hydroquinone was supplied to the decanter at a rate of 2 ml/hr for inhibiting the polymerization. The rate of the reflux to the first distillation column was controlled by means of the reflux pump so as to keep the interface between the two separated layers constant. Thus, methanol containing 1.2% of methyl methacrylate, 0.5% of water, and 470 ppm of methyl isobutyrate was obtained from the bottom of the second distillation column at a rate of 612 g/hr. The amount of methyl isobutyrate in this methanol was about 80% of that in the feed to the first distillation column. The bottom liquid in the form of two separated layers was withdrawn from the still of the first distillation column and separated in the decanter. Thus, methyl methacrylate containing 1.6% of water and 380 ppm of methyl isobutyrate could be obtained at a rate of 188 g/hr, while water containing 0.74% of methyl methacrylate was withdrawn at a rate of 54 g/hr.

EXAMPLE 2

A distillation system comprising a combination of the following first and second distillation columns as shown in the accompanying drawings was used in this Example: The first column is an Oldershaw type column having 60 plates and an inner diameter of 32 mm, and is provided with a feed inlet at the 20th stage from the top and with a water-separator at the 50th stage. This water-separator is provided for continuously separating the aqueous layer from the liquid flowing down in the distillation column which liquid contains two separated layers, because the aqueous layer and the methyl methacrylate layer are separated in the stripping section. The first distillation column is provided with a decanter to receive the distillate from the first column, which decanter is a glass vessel equipped with a water cooling jacket, and with a pipe and a pump through which the upper liquid of the two layers separated in the decanter is returned to the first distillation column. Said decanter is also equipped with a means for sending the lower methanol layer of said two layers via a liquid level gauge by means of a regulated pump to the second distillation column, said level gauge and regulated pump being for maintaining the interface between said two layers at a constant level. The second distillation column is also an Oldershaw type column having 50 plates and an inner diameter of 32 mm, and is provided with a feed inlet at the 20th stage from the top.

In said distillation system, 43 g of hexane was present, and distillation was effected while supplying a feed mixture to the first column at a rate of 166.5 g/hr, said feed mixture having a composition of 26.46% of methyl methacrylate, 66.19% of methanol, 7.28% of water, and 0.07% of methyl isobutyrate and having added thereto 0.05% of phenothiazine. During the distillation, the temperatures at the top, the bottom, and the feed stage of the first distillation column were 50° C., 106° C. and 65° C., respectively, and hexane was not present below the feed stage. The temperatures at the top and the bottom of the second distillation column were 49° C. and 67° C., respectively. The reflux ratio was set to 2.0, the temperature of the decanter for separating two layers was kept at 3° C. by circulating cold water in the jacket, and methanol containing 5% of hydroquinone was supplied to the decanter for separating two layers at a rate of 2 ml/hr for inhibiting the polymerization. The rate of the reflux to the first distillation column was controlled by means of the reflux pump so as to keep the interface between the two separated layers at a constant level. Thus, methanol containing 1.76% of methyl methacrylate, 0.91% of water, and 950 ppm of methyl isobutyrate was obtained from the bottom of the second distillation column at a rate of 110 g/hr, and methyl methacrylate containing about 130 ppm of methanol and 150 ppm of methyl isobutyrate was obtained from the bottom of the first distillation column at a rate of 42 g/hr, while water containing 2.2% of methyl methacrylate, 2.6% of methanol, and 70 ppm of methyl isobutyrate was withdrawn from the decanter of the first distillation column at an average rate of about 12 g/hr.

EXAMPLE 3

Distillation was carried out in the same manner as in Example 2, except that a water-separator was attached to the 40th stage from the top of the first distillation column, with the result that the methyl isobutyrate content in the methyl methacrylate obtained from the bottom of the first distillation column was about 70 ppm.

COMPARATIVE EXAMPLE 1

Distillation was carried out in the same manner as in Example 2, except that the amount of hexane present in the distillation system was 55 g. In this case, the temperature at the feed stage of the first distillation column was 51° C., which indicates that a considerable amount of hexane was present in the feed stage. The methyl isobutyrate content in the methyl methacrylate obtained from the bottom of the first distillation column was 2,500 ppm, and the methanol obtained from the bottom of the second distillation column was found to contain 50 ppm of methyl isobutyrate, 0.2% of methyl methacrylate, and 3.2% of water.

EXAMPLE 4

Distillation was carried out in the same manner as in Example 2, except that 35 g of cyclohexane was substituted for the 43 g of hexane and the temperature of the decanter was 10° C. In this case, the temperatures at the top, the feed stage, and the bottom of the first distillation column were 54.5° C., 65° C. and 105° C., respectively, and cyclohexane was not present below the feed stage. The temperatures at the top and the bottom of the second distillation column were 53° C. and 67° C., respectively. The methyl isobutyrate content in the methyl methacrylate obtained from the bottom of the first distillation column was 200 ppm, and the methanol obtained from the bottom of the second distillation column was found to contain 930 ppm of methyl isobutyrate, 1.5% of methyl methacrylate, and 2.0% of water.

EXAMPLE 5

Under the same conditions as in Example 2, except that the first distillation column was modified in that the feed inlet was moved to the 30th stage from the top and the water-separator attached to the 50th stage was removed, distillation was effected while supplying a mixture at a rate of 152 g/hr, said mixture having a composition of 27.5% of methyl methacrylate, 72.5% of methanol, and 0.05% methyl isobutyrate and having added thereto 0.03% of hydroquinone. In this case, the temperatures at the top, the feed stage, and the bottom of the first distillation column were 50° C., 66° C. and 105° C., respectively, and methyl methacrylate containing 180 ppm of methyl isobutyrate and a trace of methanol was obtained from the bottom thereof at a rate of 42 g/hr. The temperatures at the top and the bottom of the second distillation column were 50° C. and 67° C., respectively, and methanol which contained, on the average, 620 ppm of methyl isobutyrate and 1.3% of methyl methacrylate was obtained from the bottom thereof at a rate of 110 g/hr.

EXAMPLE 6

Under the same conditions as in Example 1, except that the content of methyl isobutyrate in the feed mixture fed to the first distillation column was changed to 3,400 ppm, distillation was effected. Methanol containing 1.1% of methyl methacrylate, 0.45% of water and 3,900 ppm of methyl isobutyrate was obtained from the bottom of the second distillation column at substantially the same rate as in Example 1. The proportion of the methyl isobutyrate contained in the methanol distilled out to the feed was 82%. The bottom liquid containing two liquid phases was withdrawn from the still of the first distillation column into the decanter, wherein the two liquid phases were separated to obtain methyl methacrylate containing 1.5% of water and 2,100 ppm of methyl isobutyrate and water containing 0.8% of methyl methacrylate at substantially the same rates as in Example 1.

EXAMPLE 7

Using the same distillation apparatus as in Example 1 and the same feed mixture as in Example 1 except that the amount of methyl isobutyrate contained was 1,700 ppm, distillation was conducted under the conditions that the temperature of the decanter was kept at 6° C. and the resident amount of hexane and distillation conditions were controlled so that the temperature in the 5th stage from the top was 55° C. The temperatures at the top, the feed stage and the bottom of the first distillation column were 50° C., 67° C. and 87° C., respectively, and the temperatures at the top, the feed stage and the bottom of the second distillation column were 50° C., 56° C. and 67° C., respectively. From the bottom of the second distillation column, there was obtained methanol containing 0.8% of methyl methacrylate, 0.6% of water and 1,950 ppm of methyl isobutyrate, and the proportion of methyl isobutyrate removed was 82%. The methanol content in the hexane layer in the decanter at that time was 6.3%.

EXAMPLE 8

Distillation was conducted under the same conditions as in Example 7, except that the temperature of the decanter was kept at 10° C., to obtain methanol containing 0.7% of methyl methacrylate, 0.6% of water and 1,900 ppm of methyl isobutyrate from the bottom of the second distillation column. The proportion of methyl isobutyrate removed was 80%. The methanol content in the hexane layer in the decanter at that time was 7.2%.

COMPARATIVE EXAMPLE 2

Distillation was conducted under the same conditions as in Example 7, except that the temperature of the decanter was kept at 15° C., to obtain methanol containing 0.4% of methyl methacrylate, 0.8% of water and 1,350 ppm of methyl isobutyrate from the bottom of the second distillation column. The proportion of methyl isobutyrate removed was 57%. The methanol content in the hexane layer in the decanter at that time was 10.8%.

COMPARATIVE EXAMPLE 3

Distillation was conducted under the same conditions as in Example 7, except that the temperature of the decanter was kept at 20° C., to obtain methanol containing 0.3% of methyl methacrylate, 0.8% of water and 750 ppm of methyl isobutyrate from the bottom of the second distillation column. The proportion of methyl isobutyrate removed was 32%. The methyl methacrylate obtained from the bottom of the first distillation column contained 5,100 ppm of methyl isobutyrate. The methanol content in the hexane layer in the decanter at that time was 15%.

EXAMPLE 9

Distillation was conducted under the same conditions as in Example 7, except that the temperature at the 5th stage from the top of the first distillation column was kept at 60° C., to obtain methanol 1.2% of methyl methacrylate and 2,000 ppm of methyl isobutyrate from the bottom of the second distillation column, and the proportion of methyl isobutyrate removed was 85%.

EXAMPLE 10

Distillation was conducted under the same conditions as in Example 7, except that the temperature at the 5th stage from the top of the first distillation column was kept at 62° C., to obtain methanol containing 2.1% of methyl methacrylate and 2,100 ppm of methyl isobutyrate from the bottom of the second distillation column. The proportion of the methyl isobutyrate removed was 89%.

What is claimed is:

1. In the process for purifying methyl methacrylate by feeding a feed mixture containing methanol, methyl methacrylate and 0.05 to 2% by weight, based on the weight of the methyl methacrylate, of methyl isobutyrate to a first distillation column, subjecting the same to distillation therein in the presence of a saturated hydrocarbon having 6 or 7 carbon atoms above the feed stage while distilling out an azeotropic mixture of said saturated hydrocarbon and the methanol, condensing the azeotropic mixture from the first distillation column, sending the resulting condensate to a decanter to separate it into a layer consisting mainly of the hydrocarbon and a layer consisting mainly of methanol, returning the layer consisting mainly of the hydrocarbon to the top of the first distillation column, feeding the layer consisting mainly of the methanol to a second distillation column, distilling the hydrocarbon dissolved in the methanol layer, together with a part of the methanol, out of the top of the second column, condensing and sending it to the above-mentioned decanter, recovering methanol from the bottom of the second distillation column, and recovering methyl methacrylate from the bottom of the first distillation column, the improvement which comprises
   (1) cooling said decanter to 0°–13° C. to conduct the layer-separation,
   (2) controlling the amount of the hydrocarbon resident in the upper part of the first distillation column so that a small amount of methyl methacrylate is also distilled out of the top of the first distillation column, and
   (3) feeding the layer consisting mainly of methanol layer-separated in the above decanter, to the second distillation column having distillation stages above the feed stage, and returning a part of the distillate from the top of the second distillation column to the top of the second distillation column, thereby recovering methyl isobutyrate and a small amount of methyl methacrylate along with methanol from the bottom of the second distillation column, and separating methanol and methyl isobutyrate from the feed mixture to the first distillation column.

2. In the process for purifying methyl methacrylate by feeding a feed mixture containing methanol, methyl methacrylate, water and 0.05 to 2% by weight, based on the weight of the methyl methacrylate, of methyl isobutyrate to a first distillation column, subjecting the same to distillation therein in the presence of a saturated hydrocarbon having 6 or 7 carbon atoms above the feed stage while distilling an azeotropic mixture of said saturated hydrocarbon and methanol out of the top, condensing the azeotropic mixture from the first distillation column, sending the resulting condensate to a decanter to separate it into a layer consisting mainly of the hydrocarbon and a layer consisting mainly of methanol, returning the layer consisting mainly of the hydrocarbon to the top of the first distillation column, feeding the layer consisting mainly of the methanol to a second distillation column, distilling the hydrocarbon dissolved in the methanol layer, together with a part of the methanol, out of the top of the second column, condensing and sending it to the above-mentioned decanter, recovering methanol from the bottom of the second distillation column, separating a mixture of $H_2O$ and methyl methacrylate at the bottom of the first distillation column into a layer consisting mainly of methyl methacrylate and a layer consisting mainly of water, withdrawing said water layer to recover the methyl methacrylate, and recovering methyl methacrylate from the bottom of the first distillation column, the improvement which comprises
   (1) cooling said decanter to 0°–13° C. to conduct the layer-separation,
   (2) controlling the amount of the hydrocarbon resident in the upper part of the first distillation column so that a small amount of methyl methacrylate is also distilled out of the top of the first distillation column, and
   (3) feeding the layer consisting mainly of methanol layer-separated in the above decanter, to the second distillation column having distillation stages above the feed stage, and returning a part of the distillate from the top of the second distillation column to the top of the second distillation column, thereby recovering methyl isobutyrate and a small amount of methyl methacrylate along with methanol from the bottom of the second distillation column, and separating methanol, water and methyl isobutyrate from the feed mixture to the first distillation column.

3. The process according to claim 2, wherein a water-separator is placed between the feed stage and the bottom of the first distillation column, the liquid in the lowest stage of the distillation column which is positioned above the said water-separator is sent to the water-separator, and separated therein into a layer consisting mainly of methyl methacrylate and a layer consisting mainly of water, the layer consisting mainly of water is withdrawn continuously, the layer consisting mainly of methyl methacrylate is sent to the highest stage of the distillation column which is positioned below the said water-separator, the vapor from the top of the distillation column below the water-separator is introduced into the lowest stage of the distillation column above the water-separator, whereby substantially anhydrous methyl methacrylate is obtained from the bottom of the first distillation column.

4. A process according to claim 1, wherein the saturated hydrocarbon is hexane.

5. A process according to claim 2, wherein the saturated hydrocarbon is hexane.

* * * * *